United States Patent
Frische et al.

(10) Patent No.: US 6,471,640 B1
(45) Date of Patent: Oct. 29, 2002

(54) ENDOSCOPE OPTICS WITH DEVICE COUNTERACTING LENS-ELEMENT SHIFTING

(75) Inventors: Holger Frische, Buchholz (DE); Jens Peter Wulfsberg, Neritz (DE); Michael Weber, Hamburg (DE)

(73) Assignee: Olympus Winter & IBE GmbH, Hamburg (DE)

(*) Notice: Subject to any disclaimer, the term of this patent is extended or adjusted under 35 U.S.C. 154(b) by 0 days.

(21) Appl. No.: 09/700,686

(22) PCT Filed: Feb. 26, 2000

(86) PCT No.: PCT/EP00/01610
§ 371 (c)(1),
(2), (4) Date: Nov. 17, 2000

(87) PCT Pub. No.: WO00/57232
PCT Pub. Date: Sep. 28, 2000

(30) Foreign Application Priority Data

Mar. 20, 1999 (DE) .......................... 199 12 656

(51) Int. Cl.⁷ ................................ A61B 1/005
(52) U.S. Cl. .................. 600/138; 359/434; 359/435; 600/139
(58) Field of Search ................ 600/138, 139; 359/434, 435

(56) References Cited

U.S. PATENT DOCUMENTS

| 4,148,550 A | | 4/1979 | MacAnally |
| 5,760,976 A | | 6/1998 | DeLaMatyr et al. |
| 6,083,152 A | * | 7/2000 | Strong ........................ 600/139 |

FOREIGN PATENT DOCUMENTS

| DE | 38 39 364 A1 | 5/1990 |
| DE | 39 12 720 A1 | 10/1990 |
| DE | 196 30 666 C1 | 11/1997 |
| DE | 197 42 454 A1 | 4/1999 |
| GB | 2 099 174 A | 12/1982 |

* cited by examiner

*Primary Examiner*—Stephen M. Hepperle
(74) *Attorney, Agent, or Firm*—Rankin, Hill, Porter & Clark LLP

(57) ABSTRACT

An endoscopic optics fitted with lens elements and securing device to secure the element positions against shifting in case of being impacted. The securing device is a circumferentially expansible tube that jointly encloses, at least at one abutment surface, the adjoining ends of two lens elements while being of a lesser inside diameter than the outside diameter of the lens elements and being permanently prestressed against them.

12 Claims, 4 Drawing Sheets

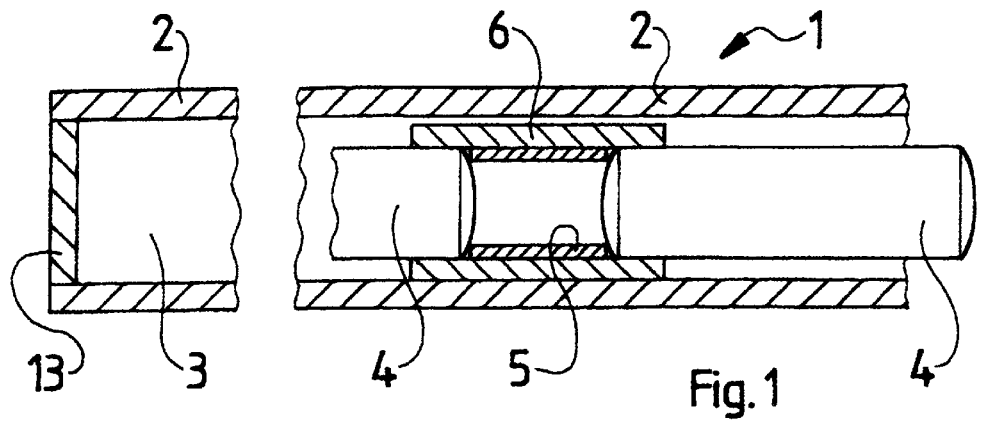
Fig. 1
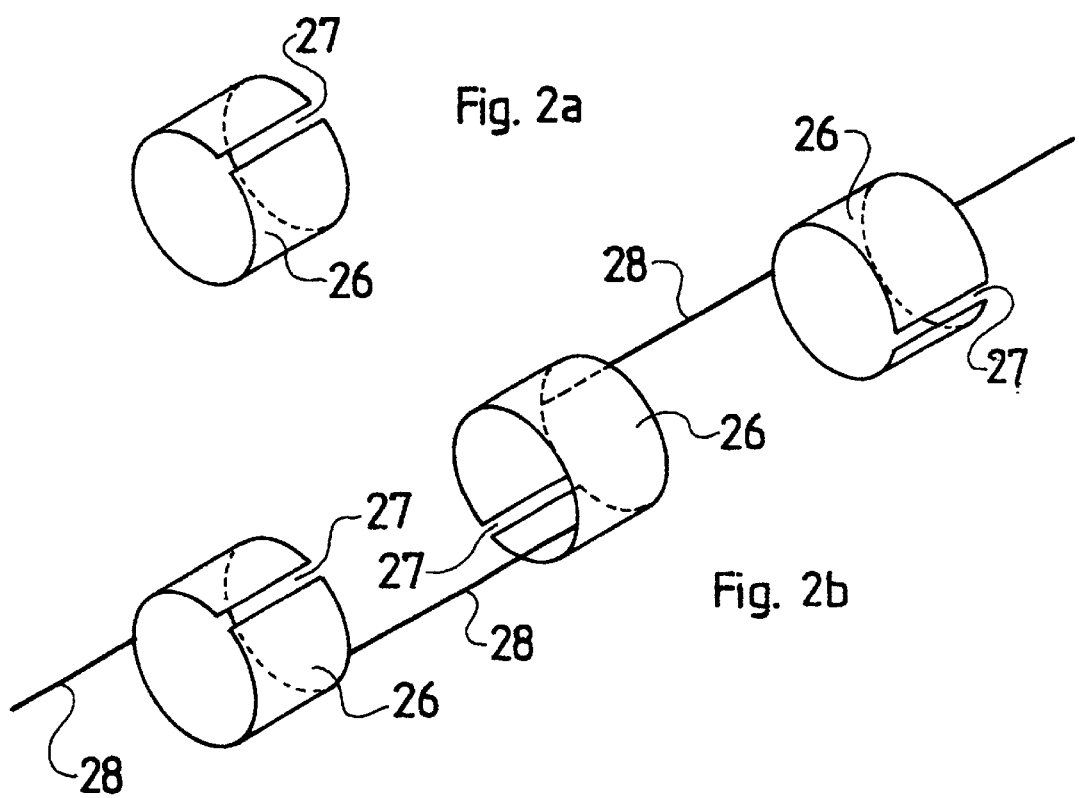
Fig. 2a
Fig. 2b
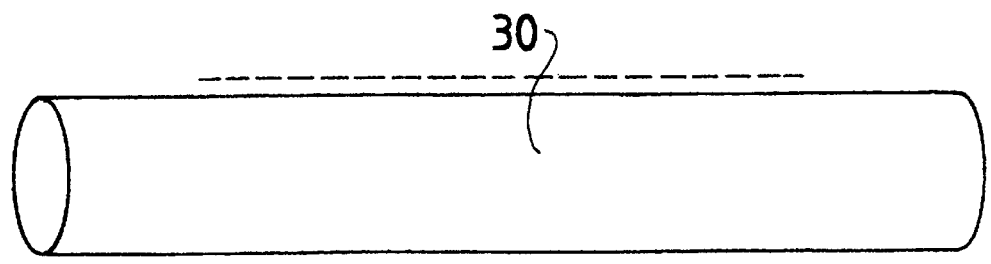
Fig. 3

ENDOSCOPE OPTICS WITH DEVICE COUNTERACTING LENS-ELEMENT SHIFTING

BACKGROUND OF THE INVENTION

FIELD OF THE INVENTION

The present invention relates to an endoscope optics fitted with lens elements and having a securing device to secure the position of the lens elements against shifting on account of impacts.

Such endoscope optics are used, in particular, in medical endoscopes. They comprise a configuration of several lens elements, typically a set of rod lenses acting as optical relays and a set of objective lens elements at the distal ends of the rod lenses. The set of objective lens elements are typically provided together with the rod lenses as an integrated unit. Herein "rod lens" denotes a thick, cylindrical lens fitted with its optical surfaces at each rod end and transmitting the images axially. An ocular, typically mounted apart from the set of rod lenses, is mounted at the proximal end of this set. The rod lens elements and the objective lens elements typically are mounted inside a system tube. The system tube aligns the lens elements and is hermetically sealed, for instance by means of windows, as required in steam sterilization in medical applications.

Such an endoscope should be highly flexible in order to permit insertion in an easily bent manner into the body ducts. The sensitive rod lenses must be protected against breaking. Typically, radial play is provided when mounting the lens elements in a system tube in order that the elements do not break when the tube is being bent.

The lens elements must be secured in their mutual configuration to assure good endoscopic optic quality. In other words, the lens elements must be affixed to each other at axially defined spacings and they must also be radially fixed. Securing devices for such purpose are known. Conventionally, the lens elements rest radially against the system tube and are axially spaced apart by spacer stubs mounted between them.

In case of impact on the endoscope optics, for instance if the endoscope falls from a table onto the floor, the lens elements may shift on account of the deceleration forces they experience. In the process, the lens elements may tip, which would entail shifting the optics direction of viewing. However, the lens elements may also rotate, with the same result, because most mass-produced rod lenses exhibit a deviation between the optic and geometric axes.

A securing device is required to prevent such effects. One such securing device is known from the post-published German patent application 19,742,454.6-51. In this design the rod lenses are mounted in a stable position and at a controlled oblique position using tubular spacers. The rod lenses in this design will always return to the stable position even after having undergone impacts. However, this securing device does not adequately prevent rotation of the lens elements it holds.

A design disclosed in the German patent document 39 12 720 C2 replaces the system tube by a shrink tube. The shrink tube is larger than required before shrinkage in order to permit easy insertion of the lens elements therein. After shrinkage, the shrink tube secures the lens elements by firmly locking them radially. As a result, the lens elements are permanently well configured one with another and, furthermore, they are secured against rotation. However, this design incurs the drawback of the cumbersome shrinkage process and of the need to use specific shrinking plastics, which exhibit other material properties that are interfering. Also, such an optics assembly cannot be subsequently repaired but can only be exchanged as a whole. Moreover, the shrinkage material used is heat sensitive and generally not appropriate for steam sterilization. Most of all, permanent securing of the lens elements is not assured by this material because of material tolerances, manufacturing tolerances or the effects of subsequent thermal influences. If the materials affixing force drops somewhat, the lens elements will become loose and can be shifted.

SUMMARY OF THE INVENTION

The objective of the present invention is to fit an endoscope optics of the aforementioned type with a securing device, wherein the securing device is easily installed, repairable, and permanently secures the lens elements.

The present invention is based on the insight that the impact-resistance of the optics can be assured already by holding the ends of the lens elements mutually aligned and non-rotatable at each abutment surface. This goal is reached in the present invention using a tube that is present at least at one abutment surface. The tube is widened at an end from a diameter less than that of the rod lenses. The tube will elastically and permanently grip the ends of the lens elements. The tube may be housed, with play, in the system tube to assure that the optics are rupture-safe when being bent. Such a tube is able to yield slightly in a resilient or elastic manner in the case of impacts, thus saving the components from rupture. The tube will also allow thermal expansions of the lens elements, while nevertheless keeping them mutually axially aligned and non-rotatable. When the tube is widened, the lens elements are easily installed or easily exchanged for repairs. The tube mutually securing the lens elements in this manner keeps an assembly together and, as a result, the pairs of lens elements or the full lens of the endoscope optics can be handled as one unit. For instance, the pairs of lens elements or the entire endoscope optics can be inserted into a system tube or another installation site. Because the radially resilient securing device also retains axially, tubular spacers securing the axial spacing between the lens elements may be eliminated.

A securing tube can mutually secure two lens elements at their joint or interface to assure their essential optical alignment. However, in accordance with other aspects of the present invention, the tube may also run completely across the secured lens elements to protect them even better against mutual tilting.

In further accordance with the present invention, the tube advantageously assumes the form of a hose made of a circumferentially elastic material, for instance an elastomer or the like. Such a hose must be circumferentially widened to allow insertion of the stack of lens elements. Insertion may be facilitated, by using compressed air to pressurize the inside of the hose or, advantageously, by externally applying a vacuum to the hose.

Alternatively, and according to other aspects of the present invention, the tube may be in the form of a pullover stocking such as is illustratively known form the German patent document 19 630 666 A1. Such a pullover stocking can be manufactured in its narrow mode. In this case, the stocking must be widened by axial pressure to install the lens elements. After being released, the stocking resumes its narrow configuration and wraps the lens elements again.

In another embodiment, the stocking also may be manufactured in the wide mode. In this case, following insertion of the lens elements the stocking may be axially tensioned in order to tightly enclose the lens elements. The stocking would thereafter require tensioning to maintain in its final assembly position.

Alternatively, the tube includes a longitudinal slot and is made of a flexurally elastic material. The tube is widened at the slot to permit insertion of the stack of lens elements. After being released, the tube will elastically close around the lens elements.

In accordance with other features of the invention, the tube is formed as a strip coil. Such a strip coil offers enormous cost advantages. Moreover, a strip coil offers substantial installation advantages. A strip coil normally in a narrow configuration can be widened, to permit insertion of the lens elements, by seizing and oppositely rotating the ends of the strip coil. Upon being released, the coil encloses the elements in a radially inward resilient manner with excellent securing efficacy. In its advantageous metallic embodiment, the coil is exceedingly well suited for long life under autoclaving. Another essential advantage offered by the strip coil is that, following rotational widening and release, the restoring force is not only radial but also in the longitudinal direction. Accordingly the coil not only secures the lens elements against tipping and rotation, but also assures their axially resilient support, without need for a separate device. If, in this manner, the stack of lens elements is axially prestressed, then special means, for instance the conventional tubular spacers, will be required to secure the axial gaps between the lens elements.

The tubes of some embodiments of the present invention may consist of flexural materials such as plastics. However, these tubes may alternatively and advantageously be made of a metal such as spring steel. The metal design is highly reliable under heat (for instance autoclaving) and also offers long life.

In accordance with other features of the invention, a slotted tube may be advantageously provided with a slot running parallel to the tube axis. This design offers simplicity, the slot being opened using simple means to insert the lens elements.

Such a slot can be very narrow and, as a result, the tube in its securing mode will almost entirely enclose the lens elements. However, a very wide slot, that is one for which the tube encloses the lens elements only slightly more than 180° still assures that the securing tube will hold the elements while also allowing, by opening the slot slightly more, to insert the lens elements sideways. Accordingly, the elements need not be inserted from the tube ends as they are in conventional assembly. The wide-open slot moreover allows accurately adjusting the elements by a simple, lateral intervention into the tube, both in the axial and in the rotational direction. Such adjustment, for instance, permits optimal matching of the lens elements to each other wherein the optic and geometric axes do not coincide.

As already mentioned above, the tube of the invention might couple every two lens elements only at abutment surfaces or individual sets of lens elements. In accordance with further features of the present invention, all the lens elements of the endoscope optics can be mounted, aligned and secured in one tube. Provided that the tube is appropriately designed, for instance as a continuous longitudinally slotted, dimensionally stable tube, the elements can be processed further.

The securing tube according to the present invention may secure mutually the lens elements of a multi-element lens, or also the objective lens, relative to the adjoining rod lens. When configuring all the lens elements of the endoscope optics in one tube, the objectives lens elements also are advantageously aligned and secured within the same configuration.

When the endoscope optics are fitted with a system tube, the circumferentially expansible tube of the invention secures the lens elements against axial and/or radial shifts, in particular when being subjected to impacts, and the assembled tube rests directly in resilient manner against the lens elements. To avert flexurally loading the lens elements when bending the system tube, a radial play is provided such that some bending of the system tube is feasible without thereby stressing the lens elements to rupture.

BRIEF DESCRIPTION OF THE DRAWINGS

These and further features of the invention will be apparent with reference to the following description and drawings, wherein:

FIG. 1 is a longitudinal section of the endoscope optics, including a tube segment securing an abutment surface, FIG. 2a is a perspective of a securing device of FIG. 1 in the form of a slotted metal tube, FIG. 2b is a perspective of several tubes of FIG. 2a that are mutually and longitudinally connected by strips, FIG. 3 is a perspective of an elastic hose.

DETAILED DESCRIPTION OF THE PREFERRED EMBODIMENTS

Figure 4A:
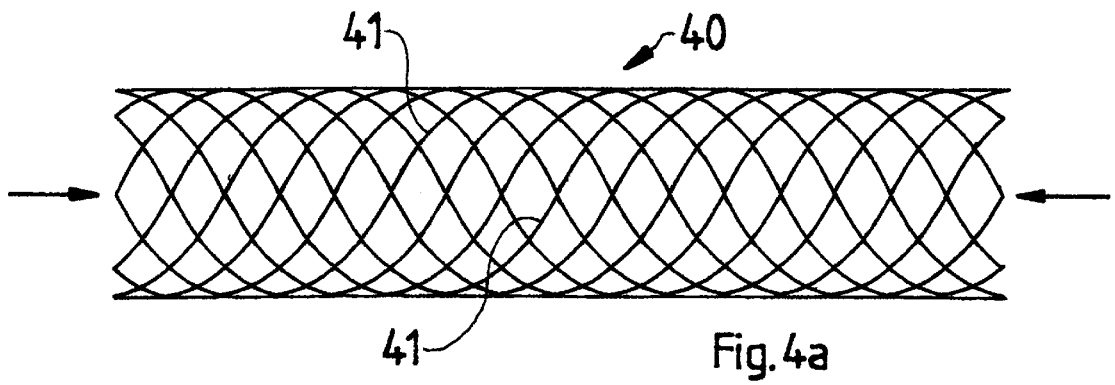
FIGS. 4a, 4b show a perspective side view of a securing device in the form of a pullover stocking in its wide mode (FIG. 4a) and in its narrow mode (FIG. 4b)

FIG. 1 shows a longitudinal section of an endoscope optics 1 fitted with a metal system tube 2. The system tube 2 is hermetically sealed, for instance by the window 13, at its ends, of which only one is shown. A stack of rod lenses 4, of which only two adjacent ones are shown in FIG. 1, are configured in the hermetically enclosed inner space 3 of the system tube 2 to transmit an image from an objective lens (not shown) mounted at one end of the optics to the ocular, or a camera situated there, at the other end of the optics. In a conventional configuration, the rod lenses rest axially against each other by means of a spacer tube 5. An omitted and axially operative spring mounted at one end of the system tube 2 conventionally prestresses the stack of lens elements in the axial direction in order to keep all lenses and spacers axially supporting each other.

As shown, the rod lenses are mounted with radial play relative to the system tube 2. Consequently, the tube can be bent into relatively small radii of curvature without breaking the rod lenses 4.

If the shown endoscope optics 1 is subjected to impacts, its individual elements will move against one another on account of inertia. At the shown abutment surface, there may arise relative radial shifts of the lens ends or even rotations of the lenses 4 of which the optic and the geometric axes do not necessarily coincide. Both shifts entail a jump of the optic axis. Already one such jump at one abutment surface and even more so at several results in a clearly interfering jump of the optics' sightline.

To prevent such dislocations, a securing device is provided which, in the embodiment of FIG. 1 and at the shown abutment surface, consists of a tube segment 6 enclosing the tubular spacer 5 and the end zones of the two neighboring rod lenses 4. The tubular segment 6 is elastically pre-stressed permanently and can be widened in the circumferential direction. Considering the desired securing function alone, the segment may be in the form of a rubber sleeve that, while expanded, is slipped over the abutment surface and then is released. As regards the desired autoclaving, an appropriately resilient plastic is applicable. Because the tubular segment 6 adequately retains the two secured lenses 4 in a resilient manner, the tubular spacer 5 may be eliminated and axial securing of the two lenses relative to each other may be provided by the resilient tube segment 6.

Instead of the tube segment 6 of FIG. 1, FIG. 2a shows an applicable tube segment 26 made of a resilient material, preferably a metal, and fitted with longitudinal slot 27 running from end to end through the tube segment. The inside diameter of the tube segment 26 is less at manufacture than the outside diameter of the rod lenses. Therefore, the slot 27 of the tube segment 26 will be widened, moved into the position of the tube segment 6 of FIG. 1, and then released. Thereupon, the tube segment 26 encloses resiliently and in securing manner the end zones of the neighboring rod lenses 4 at the shown abutment surface.

FIG. 2b shows that several slotted tube segments 26 of FIG. 2a may be connected by links 28. These segments are kept spaced by the links from the abutment surfaces at which the consecutive rod lenses rest against each other. In this manner, an assembly of illustratively required tube segments 26 for a system of rod lenses has been implemented. Moreover, the axial position of the tube segments 26 at the abutment surfaces has been secured. As shown, the slots 27 of the tube segments 26 and the links 28 may be relatively angularly offset in order to impart omni-directionally equal flexural behavior. When the lens elements are inserted, the assembly of the tube segments 26 results in a lens assembly that, even in the absence of an enclosing tube, as may be the case when assembling, is easy to handle.

FIG. 3 shows a securing device in the form of an elongated, inherently elastic hose 30 that can be stretched circumferentially in the manner already mentioned in relation to the tube segment 6 of FIG. 1. However, the hose 30 runs over the full length of the endoscope optics 1, that is, across all abutment surfaces in order to secure them. The inside diameter of the hose 30 when in its rest position, illustrated in solid lines, is smaller than the outside diameter of the rod lenses 4 (omitted for graphical clarity from FIG. 3). The hose can be elastically widened as far as the larger diameter, which is illustrated in dashed lines. Thereupon it is feasible to insert the rod lens system into the hose. After the hose 30 has been released, it will constrict radially to secure the rod lenses. Hose widening illustratively can be implemented by inflating the inside with compressed air or preferably by applying an external vacuum using appropriate assembly accessories.

Figure 4B:
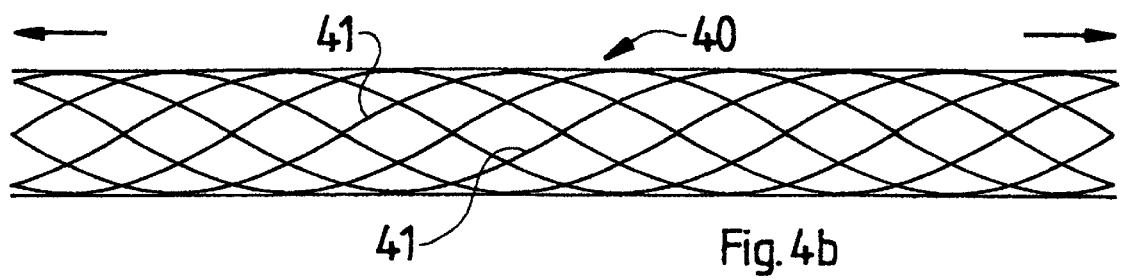

FIGS. 4a and 4b show a securing device with the same purpose as that of FIG. 3 in the form of a pullover stocking 40 consisting of a plurality of mutually crossing fibers 41. These fibers at their crossing points may be interlaced or also twisted together. A pullover stocking is adapted to widen when axially compressed in the direction of the arrow of FIG. 4a and to constrict its periphery when axially tensioned in the direction of the arrow of FIG. 4b.

The pullover stocking 40 may be prefabricated in the narrow configuration. In that case, it will be axially compressible into the wide configuration, as shown in FIG. 4a. Next a stack of lens elements (not shown) is inserted into the stocking 40. The stocking 40 is then released and constricts elastically along its circumference into the narrow configuration shown in FIG. 4b while securing the set of lens elements. In another embodiment, the pullover stocking 40 may also be prefabricated into its wide configuration as shown in FIG. 4a. Then, after the stack of lens elements has been introduced into the stocking 40, the stocking can be tensioned axially as shown by the arrows of FIG. 4b in order to elastically enclose the lens elements. Thereupon, the stocking must be installed inside the system tube as shown in FIG. 1 while tension is maintained.

Figure 5:
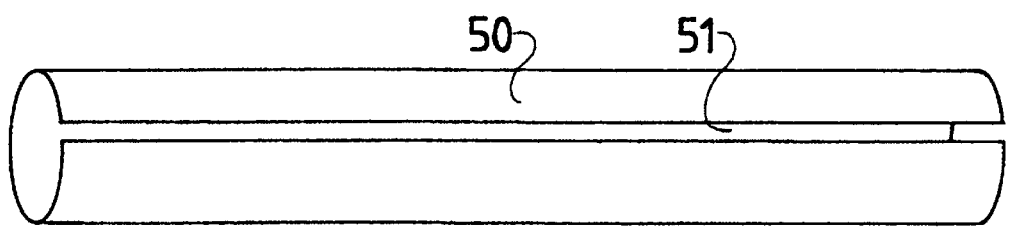
FIG. 5 is a perspective side view of a securing device in the form of an elongated, slotted metal tube.

FIG. 5 shows another embodiment of a securing device consisting of an elongated tube 50 provided with a longitudinal slot 51. Basically, this tube is designed in the manner of the tube segment 26 of FIG. 2a. However, in this embodiment the tube 50 is longer, running for instance over the full length of the optics, and thereby simultaneously secures all abutment surfaces between the rod lenses. Preferably, the tube is made of spring metal and can be filled with the stack of lens elements after the longitudinal slot has been widened. Thereafter, the stack is enclosed in securing manner by the tube 50 on account of the elastic restoring force of the tube.

Figure 6:
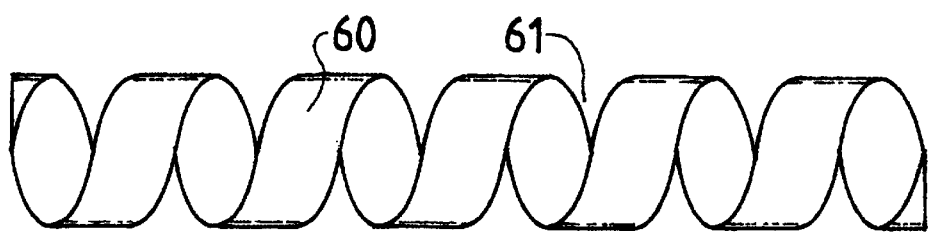
FIG. 6 is a side view of a securing device in the form of strip coil.
Figure 7:
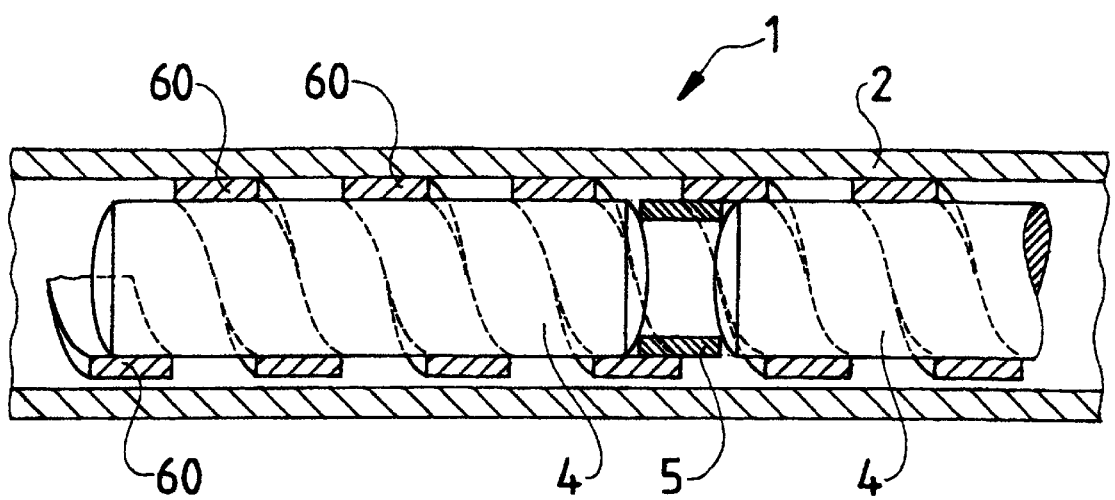
FIG. 7 is a longitudinal section of an endoscope optics fitted with the securing device of FIG. 6.

FIGS. 6 and 7 show an especially advantageous embodiment wherein the securing device is a strip coil 60. The coil encloses the stack of lens elements (not shown) as does the tube 50 of FIG. 5 or the hose 30 of FIG. 3. The strip coil 60 again runs over the full length of the stack of lens elements. However, for special purposes the strip coil 60 may only run over part of the stack length.

Like the tube 50 of FIG. 5, the strip coil 60 preferably is made of a resilient metal such as spring steel of appropriate corrosion resistance. Also, like the tube 50 of FIG. 5, the strip coil 60 is fitted with a continuous slot 61 which, however, runs helically to subtend the strip coil 60. The strip coil 60 of FIG. 6 is shown in FIG. 7 in its assembled position inside the system tube 2 of the endoscope optics 1 shown in FIG. 1. FIG. 7 shows a segment of the system tube 2 wherein two rod lenses 4 make contact with each other by means of a spacer tube 5.

The strip coil 60 is prefabricated to have an inner diameter that is less than the outer diameter of the rod lenses 4. To load the stack of lens-elements/tubular-spacers, the coil first must be widened resiliently. For that purpose it may merely be seized at both ends, for instance by a suitable means, whereupon the two ends are rotated in opposite directions to widen or enlarge the inner diameter of the strip coil 60. Not only is the circumference widened, but also there is axial elongation of the coil. Once in the widened mode, the stack of lens elements is inserted and the strip coil is released. The coil then resiliently constricts both circumferentially and longitudinally. As shown by FIG. 7, the strip coil 60 implements, at each abutment surface, the securing function around the mutually abutting ends of two rod lenses 4. Because of the longitudinal restoring force of the strip coil 60, the desired axially resilient loading of the stack of lens elements is attained and consequently the conventional end springs used for such a purpose can be eliminated. This configuration of an axially restoring force of the strip coil 60 requires the shown spacer tubes 5 situated between the lens elements 4 to secure the axial spacing between said lens elements.

As shown by FIG. 7, the outside diameter of the strip coil 60 is slightly less than the inside diameter of the system tube 2 in order to protect the sensitive rod lenses 4 against breaking when bending the system tube 2.

The devices shown in FIGS. 5 and 6 may run, as shown, over the whole length of the stack of lens elements to be secured. However, the devices may also be shorter. Illustratively and as shown in FIGS. 2a, the tube 50 of FIG. 5 may be made very short to secure only one abutment surface. This feature also applies to the strip coil 60 of FIG. 6, which can be designed to be very short to secure only one abutment surface or may be made somewhat longer to secure several abutment surfaces.

The tube 50 of FIG. 5 or the strip coil 60 of FIG. 6, however, may also be assembled in the form of several parts. In that case the slots 51 may be configured in a circumferentially offset manner in the parts adjoining in differing manner similarly to the embodiment shown in FIG. 2b. As regards the strip coil 60 of FIG. 6 and, in the case of the multi-part design, the coil winding direction may be alternating in the individual parts. Such a configuration may be advantageous in order to reduce coil rotation when the coil is expanding thermally.

Figure 8:
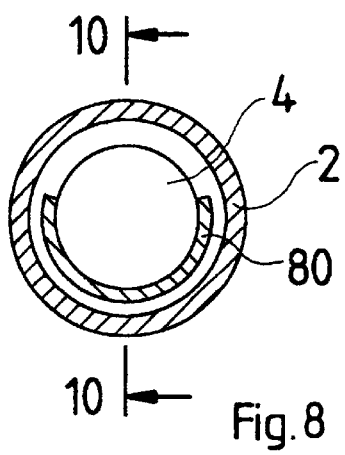
FIG. 8 is a cross-section of an endoscope optics fitted with a system tube and a securing device in the form of a broadly slotted tube.
Figure 9:
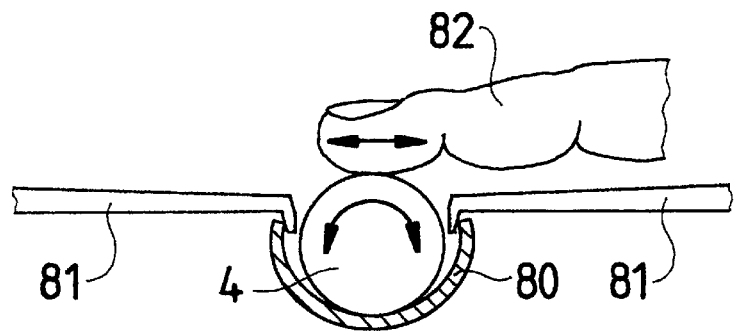
FIG. 9 is the section of FIG. 8 however without the system tube and with a slot kept widened.
Figure 10:
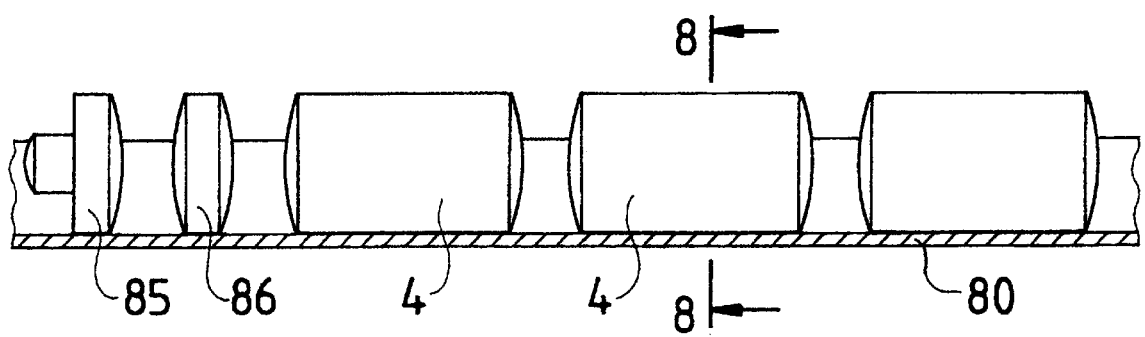
FIG. 10 is a longitudinal section along line 10—10 in FIG. 8.

FIGS. 8 through 10 show an advantageous embodiment of an endoscope using a straight, longitudinally slotted tube 80 which corresponds to the tube 50 of FIG. 5 except that the slot is much wider than the slot 51 of FIG. 5. As shown in FIG. 8, the slot in the closed configuration of the tube 80 runs over a circumferential angle somewhat less than 180°. As shown in FIG. 8, the tube 80 in its "closed" configuration still adequately encloses the lens elements 4.

As shown by FIG. 9, this wide-slotted tube 80 can be kept open using retaining tools 81 without the tube being permanently deformed, and consequently the lens elements 4 can be inserted sideways, that is according to FIG. 9 from above as if into a tub. This feature substantially simplifies installation. The lens elements 4 inserted in the manner shown in FIG. 9 are freely accessible from above and can be moved axially by the finger 82, or, as indicated by the arrows, they can be rotated. By rotating mutually oppositely, the inserted lens elements may be rotationally aligned for instance using an optical monitoring bench. This step is required when on grounds of manufacture the optic and geometric lens element axes do not coincide.

FIG. 8 shows that the lens elements 4 together with the securing tube 80 are mounted with radial play in the system tube 2, as already shown in FIG. 7, in order to reduce the danger of breaking. FIG. 8 however also shows that when using the wide-slotted tube 80, additional inside space is available in the wide slot, i.e. where the wall thickness is lacking, which is welcome for arbitrary purposes as regards the crowded cross-section of an endoscope optics. Illustratively, illuminating glass fibers, electric conductors or the like may be accommodated for which otherwise there would be no room.

FIG. 10 shows the configuration of FIG. 8 in longitudinal section, with the system tube removed for purposes of clarity. Besides the rod lenses 4, two objective lenses 85 and 86 are securely held in the tube 80 and, as a result, optic quality, very well sheltered from impact, can be assured. In other omitted embodiments, a tube such as tube 80 and which can be widened in circumferentially elastic manner may be designed to be shorter and be used to secure a single objective lens having several elements, for instance elements 85 and 86. In this design the tube for instance may also secure the first neighboring rod lens, the remaining configuration of rod lenses then being secured in some other manner.

What is claimed is:

1. An endoscope optics (1) fitted with lens elements (4, 85, 86) and with a securing device (6, 26, 30, 40, 50, 60, 80) to secure the lens elements (4, 85, 86) against shifting on account of impacts, wherein the securing device is a circumferentially expansible tube (6, 26, 30, 40, 50, 60, 80) which jointly encloses in an elastically stressed manner, at at least one abutment surface, mutually adjoining ends of two lens elements (4, 85, 86), said circumferentially expansible tube having an inside diameter that is less than an outside diameter of the lens elements so as to engage and hold said lens elements against movement in more than one direction and thereby insure axial alignment of said lens elements.

2. The endoscope optics as claimed in claim 1, wherein the tube (30, 40, 50, 60, 80) runs over the secured lens elements (4, 85, 86).

3. The endoscope optics as claimed in claim 1, wherein the tube is a hose (30) made of a circumferentially elastic material.

4. An endoscope optics (1) fitted with lens elements (4, 85, 86) and with a securing device (6, 26, 30, 40, 50, 60, 80) to secure the lens elements (4, 85, 86) against shifting on account of impacts, wherein the securing device is a circumferentially expansible tube (6, 26, 30, 40, 50, 60, 80) which jointly encloses in an elastically stressed manner, at at least one abutment surface, mutually adjoining ends of two lens elements (4, 85, 86), said circumferentially expansible tube having an inside diameter that is less than an outside diameter of the lens elements, and wherein said tube is formed as a pullover stocking (40) consisting of mutually crossing, oblique, twisted or interlaced fibers (41).

5. The endoscope as claimed in claim 1, wherein the tube (26, 50, 60, 80) is made of a flexurally elastic material and is fitted with a continuous slot (27, 51, 61) linking the tube ends.

6. The endoscope optics as claimed in claim 5, wherein the tube assumes the form of a strip coil (60).

7. The endoscope optics as claimed in claim 5, wherein the tube (26, 50, 60, 80) is made of metal.

8. An endoscope optics (1) fitted with lens elements (4, 85, 86) and with a securing device (6, 26, 30, 40, 50, 60, 80) to secure the lens elements (4, 85, 86) against shifting on account of impacts, wherein the securing device is a circumferentially expansible tube (6, 26, 30, 40, 50, 60, 80) which jointly encloses in an elastically stressed manner, at at least one abutment surface, mutually adjoining ends of two lens elements (4, 85, 86), said circumferentially expansible tube having an inside diameter that is less than an outside diameter of the lens elements, wherein the tube is made of a flexurally elastic material and is fitted with a continuous slot linking the tube ends, said slot runs parallel to an axis of the tube.

9. The endoscope optics as claimed in claim 5, wherein the slot of the tube (80) is relatively wide and subtends a circumferential angle of less than 180°.

10. The endoscope optics as claimed in claim 1, wherein the tube (30, 40, 50, 60, 80) receives all the lens elements (4, 85, 86).

11. The endoscope optics as claimed in claim 1, further comprising a distal objective lens (85, 86), wherein the tube (80) receives at least the objective lens (85, 86).

12. The endoscope optics as claimed in claim 1, fitted with the system tube (2) receiving the lens elements (4, 85, 86), wherein the circumferentially expansible tube (6, 60, 80) is mounted with radial play inside the system tube (2).

* * * * *